United States Patent
Sodeoka et al.

(10) Patent No.: US 10,995,043 B2
(45) Date of Patent: May 4, 2021

(54) METHOD FOR PRODUCING PERFLUOROALKYLATED COMPOUND

(71) Applicant: RIKEN, Wako (JP)

(72) Inventors: Mikiko Sodeoka, Wako (JP); Shintaro Kawamura, Wako (JP)

(73) Assignee: Riken, Saitama (JP)

( * ) Notice: Subject to any disclaimer, the term of this patent is extended or adjusted under 35 U.S.C. 154(b) by 302 days.

(21) Appl. No.: 16/061,449

(22) PCT Filed: Dec. 12, 2016

(86) PCT No.: PCT/JP2016/086837
§ 371 (c)(1),
(2) Date: Jun. 12, 2018

(87) PCT Pub. No.: WO2017/104589
PCT Pub. Date: Jun. 22, 2017

(65) Prior Publication Data
US 2020/0277243 A1  Sep. 3, 2020

(30) Foreign Application Priority Data

Dec. 15, 2015  (JP) .............................. JP2015-244124

(51) Int. Cl.

| | | |
|---|---|---|
| *C07B 39/00* | (2006.01) | |
| *B01J 31/22* | (2006.01) | |
| *C07C 17/266* | (2006.01) | |
| *C07C 67/293* | (2006.01) | |
| *C07D 203/24* | (2006.01) | |
| *C07D 207/08* | (2006.01) | |
| *C07D 209/10* | (2006.01) | |
| *C07D 279/02* | (2006.01) | |

(52) U.S. Cl.
CPC ............... *C07B 39/00* (2013.01); *B01J 31/22* (2013.01); *C07C 17/266* (2013.01); *C07C 67/293* (2013.01); *C07D 203/24* (2013.01); *C07D 207/08* (2013.01); *C07D 209/10* (2013.01); *C07D 279/02* (2013.01); *C07C 2601/16* (2017.05); *C07C 2602/10* (2017.05)

(58) Field of Classification Search
CPC ..... C07B 39/00; C07C 17/266; C07C 67/293; C07D 203/24
USPC .......................................................... 544/49
See application file for complete search history.

(56) References Cited

PUBLICATIONS

Charpentier et al., "Electrophilic Trifluoromethylation by Use of Hypervalent Iodine Reagents," Chem. Rev., 2015, 115:650-682.
Winter et al., "Antimalarial quinolones: Synthesis, potency, and mechanistic studies," Experimental Parasitology, 2008, 118:487-497.
Zhong et al., "Metal-free radical perfluoroalkylation of (hetero) arenes," RSC Adv., 2015, 5:6255-6258.

*Primary Examiner* — Kahsay Habte
(74) *Attorney, Agent, or Firm* — Foley & Lardner LLP

(57) ABSTRACT

Provided is a method for producing a perfluoroalkylated compound at low cost, safely and with high efficiency. A method for producing a perfluoroalkylated compound, comprising reacting a bis(perfluoroalkanoyl) peroxide with a compound having a carbon-carbon unsaturated bond and/or an aromatic ring having a hydrogen atom bonded thereto in the presence of a copper catalyst.

6 Claims, No Drawings

METHOD FOR PRODUCING PERFLUOROALKYLATED COMPOUND

CROSS-REFERENCE TO RELATED APPLICATIONS

This application is a National Stage application of PCT/JP2016/086837, filed Dec. 12, 2016, which claims priority from Japanese application JP 2015-244124, filed Dec. 15, 2015.

TECHNICAL FIELD

The present invention relates to a method for producing a perfluoroalkylated compound.

BACKGROUND ART

A perfluoroalkyl group, particularly trifluoromethyl group, is known as an important functional group contained in agricultural chemicals, medicines, functional materials and the like, and a method for efficiently introducing it into various compounds is required.

Many medicinal preparations comprising a compound having a structure in which a trifluoromethyl group is directly bonded to an aromatic ring such as a benzene ring are known, and include flufenamic acid (a nonsteroidal anti-inflammatory agent) and regorafenib (an antineoplastic drug).

Examples of a compound having a structure in which a trifluoromethyl group is bonded to an $sp^3$ carbon atom include prosulfuron (a herbicide), fluralaner (an insecticide), tolprocarb (a microbiocide), 7-methoxy-2-methyl-3-(6,6,6-trifluorohexyl)-4(1H)-quinolone (an antimalarial drug; Non Patent Literature 1).

1-Trifluoromethyl-1,2-benziodoxol-3(1H)-one (Togni reagent II) is an electrophilic trifluoromethylating reagent developed by Togni et al. It has been reported that when the reagent is used in the reaction with an olefin, a compound having a trifluoromethyl group introduced at allyl position is given (Non Patent Literature 2).

However, Togni reagent II has such problems that it is expensive and at risk of explosion.

Non Patent Literature 3 discloses that a perfluoroalkanoic anhydride (20 equivalents) was added to a urea-hydrogen peroxide complex (10 equivalents) in dichloromethane at 0° C. over 10 minutes in the absence of a metal catalyst to produce a bis(perfluoroalkanoyl) peroxide in the system, and the resulting bis(perfluoroalkanoyl) peroxide was then reacted with an aromatic compound under the same temperature condition for 1 to 2 hours to obtain the corresponding perfluoroalkylated compound. This method has been applied to various heterocyclic rings and electron-rich aromatic rings, but the yields have remained at most 50% for the heterocyclic ring and at most 36% for the benzene ring. It has also been reported that a large excess of urea-hydrogen peroxide complex is required and the reaction does not proceed at room temperature.

CITATION LIST

Non Patent Literature

Non Patent Literature 1: R. W. Winter, et al., Exp Parasitol. 118, 487 (2008).
Non Patent Literature 2: A. Togni, et al., Chem. Rev. 115, 650 (2014).
Non Patent Literature 3: S. Braese, et al., RSC Adv. 5, 6255 (2015).

SUMMARY OF INVENTION

Technical Problem

The inventors conducted the reaction using tert-butylbenzene as a substrate according to the procedure described in the experimental section of Non Patent Literature 3, but the target product was obtained only at 26% (o-:m-:p-=56:34:10) (in dichloromethane at 25° C. for 3 h).

It is an object to provide a method for efficiently producing a perfluoroalkylated compound at low cost and safely.

Solution to Problem

The summary of the present invention is as follows:

(1) A method for producing a perfluoroalkylated compound, comprising reacting a bis(perfluoroalkanoyl) peroxide with a compound having a carbon-carbon unsaturated bond and/or an aromatic ring having a hydrogen atom bonded thereto in the presence of a copper catalyst.

(2) The method according to the above (1), wherein the bis(perfluoroalkanoyl) peroxide is produced from perfluoroalkanoic anhydride and a urea-hydrogen peroxide complex.

(3) The method according to the above (1) or (2), wherein a bis(perfluoroalkanoyl) peroxide represented by formula (I):

$$Rf\text{—}CO\text{—}OO\text{—}CO\text{—}Rf \qquad (I)$$

wherein Rf represents a perfluoroalkyl group having 1 to 6 carbon atoms, is reacted with a compound represented by formula (II):

$$R^1\text{—}CH(R^2)\text{—}C(R^3)\text{=}CH_2 \qquad (II)$$

wherein $R^1$ represents an organic group, $R^2$ and $R^3$, which are the same or different, each represent a hydrogen atom or a substituted or unsubstituted $C_{1-6}$-alkyl group, to produce a perfluoroalkylated compound represented by formula (III):

$$R^1\text{—}C(R^2)\text{=}C(R^3)\text{—}CH_2\text{—}Rf \qquad (III)$$

wherein Rf, $R^1$, $R^2$ and $R^3$ are as defined above.

(4) The method according to the above (1) or (2), wherein a bis(perfluoroalkanoyl) peroxide represented by formula (I):

$$Rf\text{—}CO\text{—}OO\text{—}CO\text{—}Rf \qquad (I)$$

wherein Rf represents a perfluoroalkyl group having 1 to 6 carbon atoms, is reacted with a compound represented by formula (IV):

$$R^4\text{—}NH\text{—}X^1\text{—}C(R^3)\text{=}CH(R^5) \qquad (IV)$$

wherein $R^3$ and $R^5$, which are the same or different, each represent a hydrogen atom or a substituted or unsubstituted $C_{1-6}$-alkyl group, $R^4$ represents a substituent, $X^1$ represents a linking group having 1 to 4 chain members, and $R^5$ and $X^1$ may be linked to form a 5- to 7-membered ring together with $C(R^3)$=CH, to produce a perfluoroalkylated compound represented by formula (V):

[Formula 1]

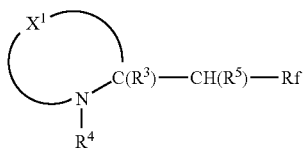
(V)

wherein Rf, $R^3$, $R^4$, $R^5$ and $X^1$ are as defined above.

(5) The method according to the above (1) or (2), wherein a bis(perfluoroalkanoyl) peroxide represented by formula (I):

Rf—CO—OO—CO—Rf     (I)

wherein Rf represents a perfluoroalkyl group having 1 to 6 carbon atoms, is reacted with a compound represented by formula (VI):

Ar—H     (VI)

wherein Ar represents a substituted or unsubstituted aromatic group, to produce a perfluoroalkylated compound represented by formula (VII):

Ar—Rf     (VII)

wherein Rf and Ar are as defined above.

(6) The method according to any one of the above (1) to (5), wherein the copper catalyst is [Cu(CH$_3$CN)$_4$]PF$_6$.

(7) A method for producing a perfluoroalkylated compound represented by formula (IX):

[Formula 2]

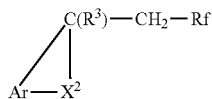
(IX)

wherein Ar is a substituted or unsubstituted aromatic group, which forms a ring in adjacent positions, Rf represents a perfluoroalkyl group having 1 to 6 carbon atoms, $X^2$ represents a linking group having 2 or 3 chain members, and $R^3$ represents a hydrogen atom or a substituted or unsubstituted $C_{1-6}$-alkyl group,
comprising reacting a bis(perfluoroalkanoyl) peroxide represented by formula (I):

Rf—CO—OO—CO—Rf     (I)

wherein Rf is as defined above,
with a compound represented by formula (VIII):

Ar—$X^2$—C($R^3$)=CH$_2$     (VIII)

wherein Ar represents a substituted or unsubstituted aromatic group, and $X^2$ and $R^3$ are as defined above,
in the absence of a copper catalyst.

(8) A method for producing a perfluoroalkylated compound,
comprising:
a first step of reacting a perfluoroalkanoic anhydride represented by formula (X):

Rf—CO—O—CO—Rf     (X)

wherein Rf represents a perfluoroalkyl group having 1 to 6 carbon atoms, with a urea-hydrogen peroxide complex at −60° C. to −10° C. to produce a bis(perfluoroalkanoyl) peroxide represented by formula (I):

Rf—CO—OO—CO—Rf     (I)

wherein Rf is as defined above, and
a second step of reacting the bis(perfluoroalkanoyl) peroxide with a compound represented by formula (VI):

Ar—H     (VI)

wherein Ar represents a substituted or unsubstituted aromatic group, at 10° C. to 100° C. to produce a perfluoroalkylated compound represented by formula (VII):

Ar—Rf     (VII)

wherein Rf and Ar are as defined above.

(9) An aziridine derivative represented by formula (V-1):

[Formula 3]

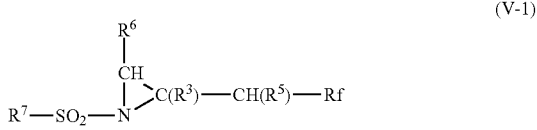
(V-1)

wherein Rf represents a perfluoroalkyl group having 1 to 6 carbon atoms, $R^3$, $R^5$ and $R^6$, which are the same or different, each represent a hydrogen atom or a substituted or unsubstituted $C_{1-6}$-alkyl group, $R^5$ and $R^6$ may be linked to form a 5- to 7-membered ring, and $R^7$ represents a substituted or unsubstituted $C_{1-6}$-alkyl group or a substituted or unsubstituted phenyl group.

Advantageous Effects of Invention

According to the present invention, a perfluoroalkylated compound can be efficiently produced at low cost and safely.

DESCRIPTION OF EMBODIMENTS

A first aspect of the present invention is a method for producing a perfluoroalkylated compound, comprising reacting a bis(perfluoroalkanoyl) peroxide with a compound having a carbon-carbon unsaturated bond and/or an aromatic ring having a hydrogen atom bonded thereto in the presence of a copper catalyst.

Preferred examples of the bis(perfluoroalkanoyl) peroxide include a compound represented by formula (I):

Rf—CO—OO—CO—Rf     (I)

wherein Rf represents a perfluoroalkyl group having 1 to 6 carbon atoms.

A second aspect of the present invention is a method for producing a perfluoroalkylated compound represented by formula (IX), comprising reacting a bis(perfluoroalkanoyl) peroxide represented by formula (I) with a compound represented by formula (VIII) in the absence of a copper catalyst.

A third aspect of the present invention is a method for producing a perfluoroalkylated compound represented by formula (VII), comprising a first step of reacting a perfluoroalkanoic anhydride represented by formula (X) with a urea-hydrogen peroxide complex at −60° C. to 0° C., preferably −60° C. to −10° C. to produce a bis(perfluoroalkanoyl) peroxide represented by formula (I), and a second step of reacting the bis(perfluoroalkanoyl) peroxide with a compound represented by formula (VI) at 0° C. to 100° C., preferably 10° C. to 100° C. to produce the perfluoroalkylated compound.

A fourth aspect of the present invention is an aziridine derivative represented by formula (V-1). The aziridine derivative represented by formula (V-1) can be converted into various compounds, and therefore is useful as a pharmaceutical intermediate or the like.

Examples of the perfluoroalkyl group having 1 to 6 carbon atoms represented by Rf in formula (I) include trifluoromethyl group, perfluoroethyl group, perfluoropropyl group, perfluoroisopropyl group, perfluorocyclopropyl group, perfluorobutyl group, perfluoroisobutyl group, perfluoro-sec-butyl group, perfluoro-tert-butyl group, perfluorocyclobutyl group, a perfluorocyclopropylmethyl group, perfluoropentyl group, perfluoro-1,1-dimethylpropyl group, perfluoro-1,2-dimethylpropyl group, perfluoroneopentyl group, perfluoro-1-methylbutyl group, perfluoro-2-methylbutyl group, perfluoro-3-methylbutyl group, a perfluorocyclobutylmethyl group, a perfluoro-2-cyclopropylethyl group, a perfluorocyclopentyl group, perfluorohexyl group, perfluoro-1-methylpentyl group, perfluoro-2-methylpentyl group, perfluoro-3-methylpentyl group, perfluoroisohexyl group, perfluoro-1,1-dimethylbutyl group, perfluoro-1,2-dimethylbutyl group, perfluoro-2,2-dimethylbutyl group, perfluoro-1,3-dimethylbutyl group, perfluoro-2,3-dimethylbutyl group, perfluoro-3,3-dimethylbutyl group, perfluoro-1-ethylbutyl group, perfluoro-2-ethylbutyl group, perfluoro-1,1,2-trimethylpropyl group, perfluoro-1,2,2-trimethylpropyl group, perfluoro-1-ethyl-1-methylpropyl group, perfluoro-1-ethyl-2-methylpropyl group or perfluorocyclohexyl group.

In the first aspect of the present invention, the term "carbon-carbon unsaturated bond" excludes any carbon-carbon double bond in an aromatic ring such as benzene ring, but includes any nonaromatic double or triple bond regardless of its conjugation with an aromatic ring, a carbonyl group, a carboxyl group or the like is present or not.

Preferred examples of the compound having the carbon-carbon unsaturated bond include:
a compound represented by formula (II):

$$R^1\text{—}CH(R^2)\text{—}C(R^3)\text{=}CH_2 \quad \text{(II)}$$

wherein $R^1$ represents an organic group, $R^2$ and $R^3$, which are the same or different, each represent a hydrogen atom or a substituted or unsubstituted $C_{1-6}$-alkyl group, and a compound represented by formula (IV):

$$R^4\text{—}NH\text{—}X^1\text{—}C(R^3)\text{=}CH(R^5) \quad \text{(IV)}$$

wherein $R^3$ and $R^5$, which are the same or different, each represent a hydrogen atom or a substituted or unsubstituted $C_{1-6}$-alkyl group, $R^4$ represents a substituent, $X^1$ represents a linking group having 1 to 4 chain members, and $R^5$ and $X^1$ may be linked to form a 5- to 7-membered ring together with $C(R^3)$=CH.

Preferred examples of the compound having an aromatic ring having a hydrogen atom bonded thereto include a compound represented by formula (VI):

$$Ar\text{—}H \quad \text{(VI)}$$

wherein Ar represents a substituted or unsubstituted aromatic group.

When the compound used as a substrate in the first aspect of the invention has both a "carbon-carbon unsaturated bond" and an "aromatic ring having a hydrogen atom bonded thereto", the reaction with the former precedes.

The second aspect of the present invention uses as a substrate a compound represented by formula (VIII):

$$Ar\text{—}X^2\text{—}C(R^3)\text{=}CH^2 \quad \text{(VIII)}$$

wherein Ar is a substituted or unsubstituted aromatic group, $X^2$ represents a linking group having 2 or 3 chain members, and $R^3$ represents a hydrogen atom or a substituted or unsubstituted $C_{1-6}$-alkyl group.

The third aspect of the present invention uses a compound represented by formula (VI) as a substrate.

The organic group represented by $R^1$ in formula (II) is not particularly limited, and includes a substituted or unsubstituted hydrocarbon group or heterocyclic group. The hydrocarbon group may contain a heteroatom such as an oxygen atom, a sulfur atom and a nitrogen atom as a chain member or in a side chain.

Examples of the hydrocarbon group include a $C_{1-20}$-alkyl group (for example, a methyl group, an ethyl group, a propyl group, an isopropyl group, a butyl group, an isobutyl group, a sec-butyl group, a tert-butyl group, a pentyl group, an isopentyl group, a hexyl group, a heptyl group, an octyl group, a nonyl group, a decyl group, an undecyl group, a dodecyl group, a tridecyl group, a tetradecyl group, a pentadecyl group, a cyclopropyl group, a cyclobutyl group, a cyclopentyl group and a cyclohexyl group), an aryl group (for example, a phenyl group, a 1-naphthyl group, a 2-naphthyl group and a tolyl group) and an aralkyl group (for example, a benzyl group and a phenethyl group). The hydrocarbon group may be substituted with one or more substituents selected from a halogen atom (for example, a fluorine atom, a chlorine atom, a bromine atom and an iodine atom), a hydroxyl group, an amino group, a mono- or dialkylamino group, $C_{1-6}$-alkoxy group (for example, a methoxy group, an ethoxy group and a propoxy group), an oxo group, a heterocyclic group and the like.

Examples of the substituted $C_{1-20}$-alkyl group include, but not limited thereto, —(CH$_2$)$_n$-Hal wherein n represents an integer of 1 to 20, and Hal represents a halogen atom (for example, a fluorine atom, a chlorine atom and a bromine atom), —(CH$_2$)$_n$—OH wherein n represents an integer of 1 to 20, and —(CH$_2$)$_{n-2}$—COCH$_3$ wherein n represents an integer of 1 to 20.

Examples of the heterocyclic group include an oxygen-containing heterocyclic group such as a furyl group.

The hydrocarbon group or heterocyclic group may be substituted with one or more substituents selected from an aromatic group, an acyl group (for example, a $C_{1-6}$-aliphatic acyl group such as a formyl group, an acetyl group, a propanoyl group, a butanoyl group, a pentanoyl group and a hexanoyl group; and an aroyl group such as a benzoyl group and a toluoyl group), an acyloxy group (for example, a $C_{1-6}$-aliphatic acyloxy group such as a formyloxy group, an acetoxy group, a propanoyloxy group, a butanoyloxy group, a pentanoyloxy group and a hexanoyloxy group; and an aroyloxy group such as a benzoyloxy group and a toluoyloxy group), a hydroxyl group, a carboxyl group, a halogen atom (such as a fluorine atom, a chlorine atom, a bromine atom and an iodine atom), a $C_{1-6}$-alkoxy group (for example, a methoxy group, an ethoxy group and a propoxy group) and the like.

Examples of the $C_{1-6}$-alkyl group represented by $R^2$, $R^3$, $R^5$, $R^6$ and $R^7$ in formulas (II), (III), (IV), (V), (V-1), (VIII) and (IX) include a methyl group, an ethyl group, a propyl group, an isopropyl group, a butyl group, an isobutyl group, a sec-butyl group, a tert-butyl group, a pentyl group, an isopentyl group, a hexyl group, a cyclopropyl group, a cyclobutyl group, a cyclopentyl group and a cyclohexyl group. The $C_{1-6}$-alkyl group may be substituted with one or more substituents selected from a halogen atom (for example, a fluorine atom, a chlorine atom and a bromine atom), a hydroxyl group, an amino group, a mono- or dialkylamino group, $C_{1-6}$-alkoxy group (for example, a methoxy group, an ethoxy group and a propoxy group), an oxo group, an aromatic group, a heterocyclic group and the like.

Examples of the substituent represented by $R^4$ in formulas (IV) and (V) include a 3,5-diphenylphenyl group, a 4-methoxyphenyl group, a 4-fluorophenyl group, a 4-ethoxycarbonylphenyl group, a piperidyl group, a mesyl group (Ms), a tosyl group (Ts), a trifluoromethanesulfonyl group (Tf), a 4-methoxybenzenesulfonyl group, a 4-fluorobenzenesulfonyl group, a 4-bromobenzenesulfonyl group and a 4-nitrobenzenesulfonyl group.

In formula (V-1), $R^3$, $R^5$ and $R^6$ preferably represents a hydrogen atom, preferred examples of the substituted or unsubstituted $C_{1-6}$-alkyl group represented by $R^7$ include a methyl group and a trifluoromethyl group, and preferred examples of the substituted or unsubstituted phenyl group include a phenyl group, a tolyl group, a 4-methoxyphenyl group, a 4-fluorophenyl group, a 4-bromophenyl group and a 4-nitrophenyl group.

The chain member(s) forming a linking group represented by $X^1$ or $X^2$ in formula (IV), (V), (VIII) or (IX) may be selected from a carbon atom, a nitrogen atom, an oxygen atom and a sulfur atom, and preferably contains a carbon atom. The linking group may have a side chain comprising, for example, the above-mentioned substituted or unsubstituted $C_{1-6}$-alkyl group, the side chain may have a spiro ring structure and a ring-fused structure such as a cycloalkane ring, a benzene ring and a heterocyclic ring. Preferred examples of the linking group include a substituted or unsubstituted alkylene group. The linking group represented by $X^1$ in formulas (IV) and (V) have 1 to 4 chain members, preferably 1 to 3 chain members.

In formulas (IV) and (V), $R^5$ and $X^1$ may be linked to form a 5- to 7-membered ring together with $C(R^3)$=CH. Examples of the compound represented by formula (IV) when $R^5$ and $X^1$ is linked to form a 6-membered ring together with $C(R^3)$=CH include a compound represented by formula (IV-1):

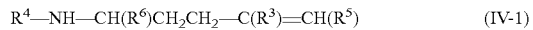

R<sup>4</sup>—NH—CH(R<sup>6</sup>)CH<sub>2</sub>CH<sub>2</sub>—C(R<sup>3</sup>)=CH(R<sup>5</sup>)    (IV-1)

wherein $R^3$ represents a hydrogen atom or a substituted or unsubstituted $C_{1-6}$-alkyl group, $R^4$ represents a substituent and $R^5$ and $R^6$ is linked to form a 6-membered ring.

Examples of the aromatic group represented by Ar in formulas (VI), (VII), (VIII) and (IX) include an aromatic hydrocarbon group such as a phenyl group, a tolyl group and a naphthyl group; and an oxygen-containing heteroaromatic group such as a furyl group.

The aromatic group may be substituted with one or more substituents selected from an aromatic group, an acyl group (for example, a $C_{1-6}$-aliphatic acyl group such as a formyl group, an acetyl group, a propanoyl group, a butanoyl group, a pentanoyl group and a hexanoyl group; and an aroyl group such as a benzoyl group and a toluoyl group), an acyloxy group (for example, a $C_{1-6}$-aliphatic acyloxy group such as a formyloxy group, an acetoxy group, a propanoyloxy group, a butanoyloxy group, a pentanoyloxy group and a hexanoyloxy group; and an aroyloxy group such as a benzoyloxy group and a toluoyloxy group), a hydroxyl group, a carboxyl group, a halogen atom (for example, a fluorine atom, a chlorine atom, a bromine atom and an iodine atom), a $C_{1-6}$-alkoxy group (for example, a methoxy group, an ethoxy group and a propoxy group) and the like.

In the first and second aspects of the present invention, the method for producing a bis(perfluoroalkanoyl) peroxide is not particularly limited, and examples of the method include a method in which a perfluoroalkanoic anhydride is reacted with a peroxide such as hydrogen peroxide, a urea-hydrogen peroxide complex, a triphenylphosphine oxide-hydrogen peroxide complex, an amine oxide-hydrogen peroxide complex, tert-butyl peroxide and peracetic acid. The bis(perfluoroalkanoyl) peroxide which has been preliminarily prepared by such a method and stored can be used, but from the viewpoint of simplification of the process and a good yield in the preparation stage, it is preferably produced in situ from an perfluoroalkanoic anhydride and a urea-hydrogen peroxide complex.

Preferred examples of the bis(perfluoroalkanoyl) peroxide include a compound represented by formula (I):

Rf—CO—OO—CO—Rf    (I)

wherein Rf represents a perfluoroalkyl group having 1 to 6 carbon atoms.

The compound (I) is preferably obtained by reacting a perfluoroalkanoic anhydride represented by formula (X):

Rf—CO—O—CO—Rf    (X)

wherein Rf is as defined above,
with a urea-hydrogen peroxide complex. At that time, the reaction temperature is preferably −60° C. to −10° C., more preferably −50° C. to −30° C. from the viewpoint of decomposition of the bis(perfluoroalkanoyl) peroxide.

In the third aspect of the present invention, for the same reason as above, in the first step, a perfluoroalkanoic anhydride represented by formula (X) is reacted with a urea-hydrogen peroxide complex at −60° C. to −10° C., preferably −50° C. to −20° C.

The equivalent ratio of the perfluoroalkanoic anhydride represented by formula (X) to the urea-hydrogen peroxide complex is generally 3:1 to 20:1, preferably 4:1 to 10:1 and more preferably from 5:1 to 10:1.

The equivalent ratio of the perfluoroalkanoic anhydride represented by formula (X) to a substrate is generally 20 to 3:1, preferably 10 to 6:1, and the equivalent ratio of the urea-hydrogen peroxide complex to the substrate is generally 5 to 1:1, preferably 3 to 1:1.

In the first, second and third aspects of the present invention, the reaction can be conducted in a solvent or in the absence of a solvent.

Examples of the reaction solvent include a halogenated hydrocarbon-based solvent such as dichloromethane, chloroform, 1,2-dichloroethane, carbon tetrachloride, 1,1,2,2-tetrachloroethane; acetonitrile, dimethylsulfoxide, and N-methylpyrrolidone.

In the first aspect of the present invention, a bis(perfluoroalkanoyl) peroxide is reacted with a compound having a carbon-carbon unsaturated bond and/or an aromatic ring having a hydrogen atom bonded thereto in the presence of a copper catalyst. In the absence of a copper catalyst, little target product is obtained and a side reaction also occurs.

The copper catalyst is not particularly limited as long as it is a salt or a complex salt of a monovalent or divalent copper. Examples of the copper catalyst include a copper (I) halide (for example, copper (I) chloride, copper (I) bromide and copper (I) iodide), copper (II) halide (for example, copper (II) chloride, copper (II) bromide, copper (II) iodide), copper (I) acetate, copper (II) acetate, copper (I) 2-thiophenecarboxylate (CuTC), copper (II) trifluoromethanesulfonate and [Cu(CH₃CN)₄]PF₆ (tetrakis(acetonitrile)copper(I) hexafluorophosphate), and preferably [Cu(CH₃CN)₄]PF₆. The amount of the copper catalyst to be used is generally 1 to 30 mol %, preferably 10 to 20 mol %.

In the first aspect of the present invention, the reaction temperature in the reaction of the bis(perfluoroalkanoyl) peroxide with the substrate compound is generally −5° C. to 100° C., preferably 0° C. to 50° C., and the reaction time is generally 2 to 24 hours, preferably 2 to 4 hours.

In the second aspect of the present invention, a bis (perfluoroalkanoyl) peroxide represented by formula (I) is reacted with a compound represented by formula (VIII) in the absence of a copper catalyst. Under the presence of the copper catalysis, only 21% of the target product is obtained and a side reaction also occurs.

In the second aspect of the present invention, the reaction temperature in the reaction of the bis(perfluoroalkanoyl) peroxide with the substrate compound is generally −5° C. to 100° C., preferably 0° C. to 90° C., and the reaction time is generally 5 minutes to 48 hours, preferably 2 to 24 hours.

In the third aspect of the present invention, from the viewpoint of efficiently producing the target product, in the second step, the bis(perfluoroalkanoyl) peroxide represented by formula (I) produced in the first step is reacted with the compound represented by formula (VI) at 0° C. to 100° C., preferably from 20° C. to 90° C. This reaction can be conducted in the absence of a copper catalyst, but it is preferably conducted in the presence of the copper catalyst.

When the nitrogen atom or the like in the product obtained by the above reaction is protected with a protecting group, deprotection can be conducted according to a conventional method if necessary.

The purification of the product obtained as described above can be conducted by a method commonly used such as column chromatography using silica gel or the like as a carrier; distillation; or a recrystallization method using hexane, chloroform, methanol, ethanol, dimethylsulfoxide or water or the mixed solvent thereof. Examples of the elution solvent for column chromatography include methanol, ethanol, chloroform, acetone, hexane, dichloromethane and ethyl acetate and a mixed solvent thereof.

The specification of the present application includes the contents described in the specification of Japanese Patent Application No. 2015-244124 which is the basis of the priority of the present application.

EXAMPLES

The present invention will be further described in detail by examples but is not to be limited by these examples.

(Example 1) Synthesis of 6,6,6-trifluoro-3-hexenyl Benzoate

[Formula 4]

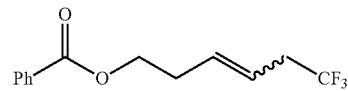

(1) To a suspension of a urea-hydrogen peroxide complex (23 mg, 0.24 mmol) in dichloromethane (0.5 mL) was slowly added trifluoroacetic anhydride (282 μL, 2.0 mmol) at −40° C. After stirring at the same temperature for 1 hour, 4-pentenyl benzoate (la) (32 mg, 0.2 mmol, concentration: 0.4 M) and [Cu(CH₃CN)₄]PF₆ (8 mg, 0.02 mmol) were added. Then, the mixture was immediately warmed to 40° C. and stirred for 3 hours. After dilution with 5 mL of ethyl acetate, the reaction was quenched with a saturated sodium thiosulfate aqueous solution followed by a saturated potassium carbonate aqueous solution. The aqueous layer was extracted with ethyl acetate three times. The combined organic phase was dried over sodium sulfate, and the solvent was evaporated. Flash column chromatography of the crude product on silica gel (ethyl acetate/hexane=5/95) afforded the target compound as colorless oil (49 mg, 95% yield, E/Z ratio=78/22).

(2) The reaction was conducted in the same manner as in (1) except the amount of dichloromethane used was changed to 0.25 mL (substrate (la) concentration: 0.2M) and the type of catalyst was changed. The results are shown in Table 1. Entry No. 2 in Table 1 corresponds to the above (1).

TABLE 1

| entry | catalyst | yield of 2a (%)$^a$ (E/Z) | recov. of 1a (%)$^a$ |
|---|---|---|---|
| 1 | [Cu(CH₃CN)₄]PF₆ | 92 (78/22) | 5 |
| 2$^b$ | [Cu(CH₃CN)₄]PF₆ | 95 (78/22)$^c$ | 4 |
| 3 | CuI | 23 (76/24)$^c$ | 48 |
| 4 | CuBr | 73 (77/23) | 49 |
| 5 | CuCl | 70 (76/24) | 20 |
| 6 | CuOAc | 82 (76/24) | 26 |
| 7 | CuTc | 34 (76/24) | 18 |
| 8 | Cu(OAc)₂ | 2 | 11 |
| 9 | FeCl₂ | 1 | 70 |
| 10 | Fe(OAc)₂ | 1 | 70 |
| 11 | Mn(OAc)₂ |  | 76 |

$^a$Yields and E/Z ratio were determined by $^1$H NMR analysis and $^{19}$F NMR analysis, respectively.
$^b$The reaction was conducted at substrate (la) concentration of 0.4 M in dichloromethane.
$^c$Isolated yield.

The results in Table 1 show that the copper catalyst, particularly [Cu(CH$_3$CN)$_4$]PF$_6$ is excellent as a catalyst for introducing a trifluoromethyl group.

On the other hand, when the reaction was conducted in the same manner as described above with no catalyst, little target compound was obtained as shown below.

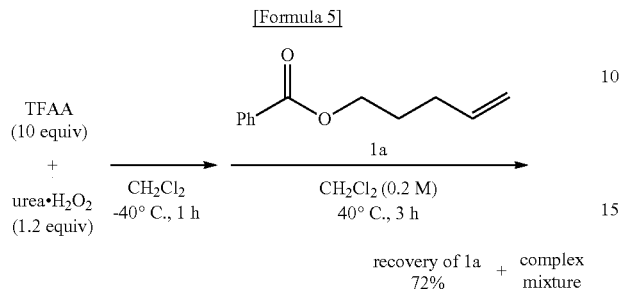

[Formula 5]

(3) The reaction was conducted as the same manner as in entry No. 1 in Table 1 of the above (2) except that the amount of copper catalyst ([Cu(CH$_3$CN)$_4$]PF$_6$) used in entry No. 1 in Table 1 of the above (2) was changed. The results are shown in Table 2. Entry No. 2 in Table 2 corresponds to entry No. 1 in Table 1.

TABLE 2

| entry | catalyst loading | yield of 2a (%) (E/Z) | recov. of 1a (%) |
|---|---|---|---|
| 1 | 20 mol % | 96 (78/22) | n.d. |
| 2 | 10 mol % | 92 (78/22) | 5 |
| 3 | 5 mol % | 88 (78/22) | 19 |
| 4 | 1 mol % | 78 (77/23) | 20 |

Even when the amount of catalyst was decreased, the target product was obtained with a good yield.

(4) The reaction was conducted as the same manner in entry No. 2 or entry No. 4 in Table 2 of the above (3) except that the amounts of trifluoroacetic anhydride (TFAA) and dichloromethane used in entry No. 2 and entry No. 4 in Table 2 of the above (3) were changed. The results are shown in Table 3. Note that the amount of urea-hydrogen peroxide complex used in entry No. 3 in Table 3 was 1.5 equivalents. Entry No. 1 and No. 2 in Table 3 corresponds to entry No. 2 and No. 4 in Table 2, respectively.

TABLE 3

| entry | amount of TFAA (equiv) | cat. loading (mol %) | conc. (M) | yield of 2a (%) (E/Z) | recov. of 1a (%) |
|---|---|---|---|---|---|
| 1 | 10 | 10 | 0.2 | 92 (78/22) | 5 |
| 2 | 10 | 1 | 0.2 | 78 (77/23) | 20 |

TABLE 3-continued

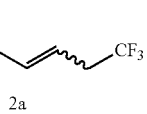

| entry | amount of TFAA (equiv) | cat. loading (mol %) | conc. (M) | yield of 2a (%) (E/Z) | recov. of 1a (%) |
|---|---|---|---|---|---|
| 3* | 10 | 1 | 0.2 | 75(78/22) | 15 |
| 4 | 10 | 1 | 0.4 | 82 (78/22) | 17 |
| 5 | 10 | 10 | 0.4 | 95 (78/22) | 4 |
| 6 | 8 | 10 | 0.4 | 73 (78/22) | 2 |

*1.5 equiv of urea·H₂O₂ was used.

(Example 2) Synthesis of Various Perfluoroalkylated Compounds

Unless stated below, various perfluoroalkylated compounds were synthesized using the conditions described in Example 1 (1). The results are shown in Table 4.

TABLE 4

| entry | starting material | product / isolated yield (E/Z)ᵃ |
|---|---|---|
| 1 | C₆H₁₃—CH=CH₂ (1b) | C₆H₁₃—CH=CH—CF₃ (2b 82% (80/20)) |
| 2ᵇ,ᶜ | 4-methylphenyl-(CH₂)₂-CH=CH₂ (1c) | 4-methylphenyl-(CH₂)₂-CH=CH-CF₃ (2c 71% (82/18)) |
| 3 | CH₃CO(CH₂)₉CH=CH₂ (1d) | CH₃CO(CH₂)₉CH=CH-CF₃ (2d 83% (79/21)) |
| 4 | Br(CH₂)₅CH=CH₂ (1d) | Br(CH₂)₅CH=CH-CF₃ (2d 92% (80/20)) |
| 5ᶜ,ᵈ | HO(CH₂)₄CH=CH₂ (1f) | HO(CH₂)₄CH=CH-CF₃ (2f 90% (73/27)) |
| 6ᶜ | Phthalimide-N-(CH₂)₃-CH=CH₂ (1g) | Phthalimide-N-(CH₂)₃-CH=CH-CF₃ (2g 93% (71/29)) |
| 7ᶜ | Ph-N(Boc)-(CH₂)₃-CH=CH₂ (1h) | Ph-N(COCF₃)-(CH₂)₃-CH=CH-CF₃ (2h 91% (76/24)) |

TABLE 4-continued

| entry | starting material | product / isolated yield (E/Z)[a] |
|---|---|---|
| 8 | Ts-NH-(CH2)3-CH=CH2 (1i) | Ts-NH-(CH2)3-CH=CH-Rf; $R_f$ = CF$_3$ (2i) 90% (72/28) |
| 9 | | $R_f$ = C$_2$F$_5$ (2i') 81% (72/28) |
| 10 | | $R_f$ = C$_3$F$_7$ (2i'') 72% (75/25) |

[a] E/Z ratio was determined by $^{19}$F NMR analysis.
[b] The reaction was conducted at a substrate concentration of 0.2 M in dichloromethane at 0° C.
[c] 20 Mol % of the catalyst was used.
[d] The crude product was treated with Et$_3$N/SiO$_2$ for hydrolysis.

(Example 3) Synthesis of Trifluoromethylated Nitrogen-Containing Heterocyclic Compound The reaction was conducted in the same manner as in Example 1 (1) except that N-tosyl-N-(4-pentenyl)amine was used as a substrate. As a result, a trifluoromethylated nitrogen-containing heterocyclic compound was obtained in a good yield (82%) as shown below.

[Formula 6]

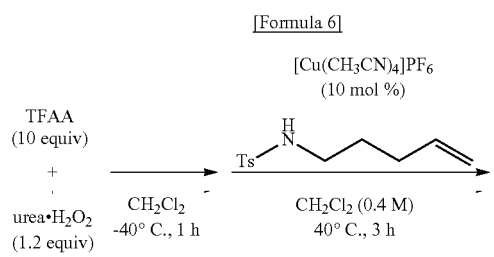

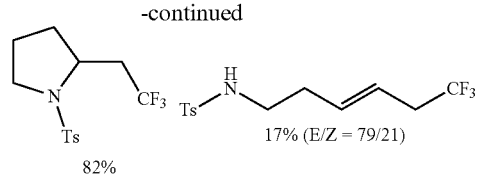

82%     17% (E/Z = 79/21)

(Example 4) Synthesis of 1-tosyl-2-(2,2,2-trifluoroethyl)aziridine

The reaction was conducted in the same manner as in Example 1 (1) by using a substrate concentration of 1.0 M, a reaction time of 7 minutes and N-tosylallylamine as a substrate. As a result, trifluoromethylated aziridine was obtained at a high yield (87%) as shown below. When the similar reaction is conducted by stirring 4 equivalents of TFAA and 1.2 equivalents of urea-hydrogen peroxide in 0.4 M dichloromethane at 0° C. for 1 hour and 10 mol % of a copper catalyst and a substrate is then added thereto and is allowed to react at 0° C. for 1 hour, the target product can be obtained at an equivalent yield (91%).

Formula 7

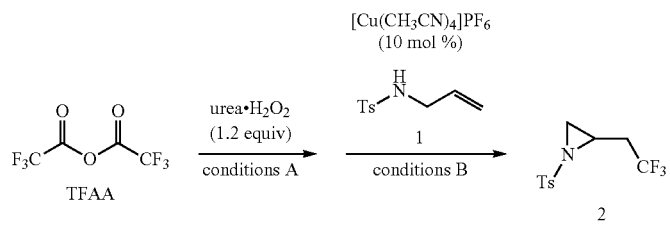

| entry | amount of TFAA | conditions A | conditions B | yield of 2 |
|---|---|---|---|---|
| 1 | 10 equiv. | CH$_2$Cl$_2$, −40° C., 1 h | CH$_2$Cl$_2$ (1.0 M), −40° C., 7 min | 87% |
| 2 | 4 equiv. | CH$_2$Cl$_2$, 0° C., 1 h | CH$_2$Cl$_2$ (0.4 M), 0° C., 1 h | 91% |

(Example 5) Synthesis of Trifluoromethylated Nitrogen-Containing Heterocyclic Compounds The following compounds can be produced as the same manner as in Example 3 or 4 except that the type of substrate is changed.

[Formula 8]

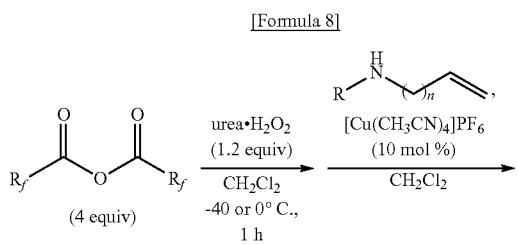

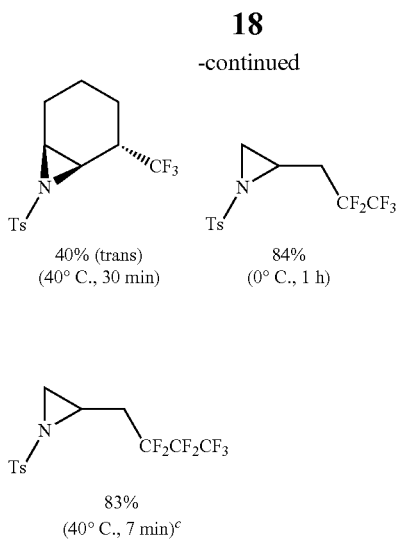

40% (trans)　　84%
(40° C., 30 min)　(0° C., 1 h)

83%
(40° C., 7 min)$^c$ pyrrolidines and indolines$^c$

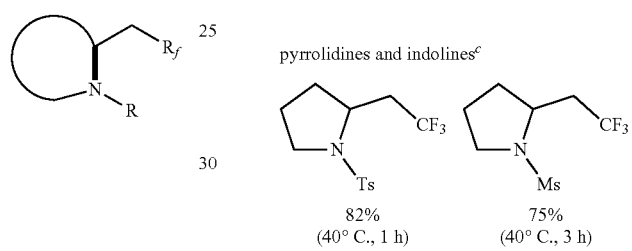

82%　　　75%
(40° C., 1 h)　(40° C., 3 h)

aziridines

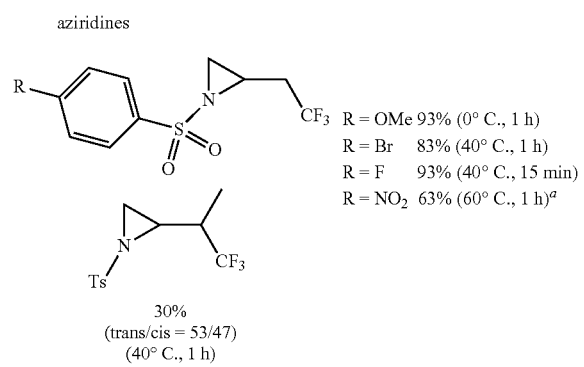

R = OMe 93% (0° C., 1 h)
R = Br　83% (40° C., 1 h)
R = F　93% (40° C., 15 min)
R = NO$_2$ 63% (60° C., 1 h)$^a$ 30%
(trans/cis = 53/47)
(40° C., 1 h)

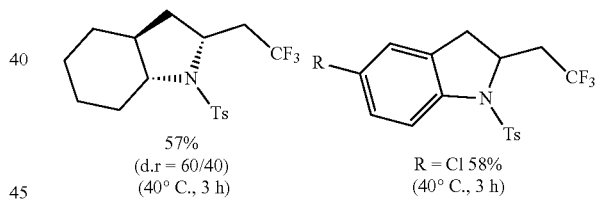

57%　　　　R = Cl 58%
(d.r = 60/40)　(40° C., 3 h)
(40° C., 3 h)

a: In 1,2-dichloroethane as a solvent at a reaction temperture of 60° C.
b: Copper catalyst: 20 mol%
c: Trifluoroacetic anhydride: 10 mol%

In the above formulas, Rf represents a perfluoroalkyl group having 1 to 6 carbon atoms, Ts represents a tosyl group, Ms represents a methanesulfonyl group, Tf represents a trifluoromethanesulfonyl group, and R represents a hydrogen atom or a substituent.

(Example 6) Derivatization of Aziridine

The aziridine product synthesized in Example 4 can be derivatized into various trifluoromethylamines by ring-opening reaction with various nucleophilic reagents. Furthermore, tetrahydroharmine and a compound having a spiroindolone skeleton which are known as a physiologically active molecule such as a medicine can be synthesized by deprotection of the tosyl group of the tryptamine product followed by Pictet-Spengler reaction.

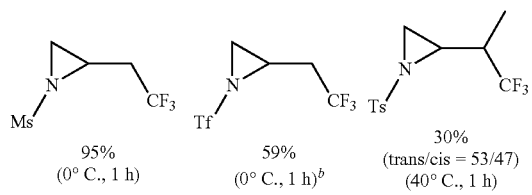

95%　　　59%　　　30%
(0° C., 1 h)　(0° C., 1 h)$^b$　(trans/cis = 53/47)
　　　　　　　　　(40° C., 1 h)

[Formula 9]

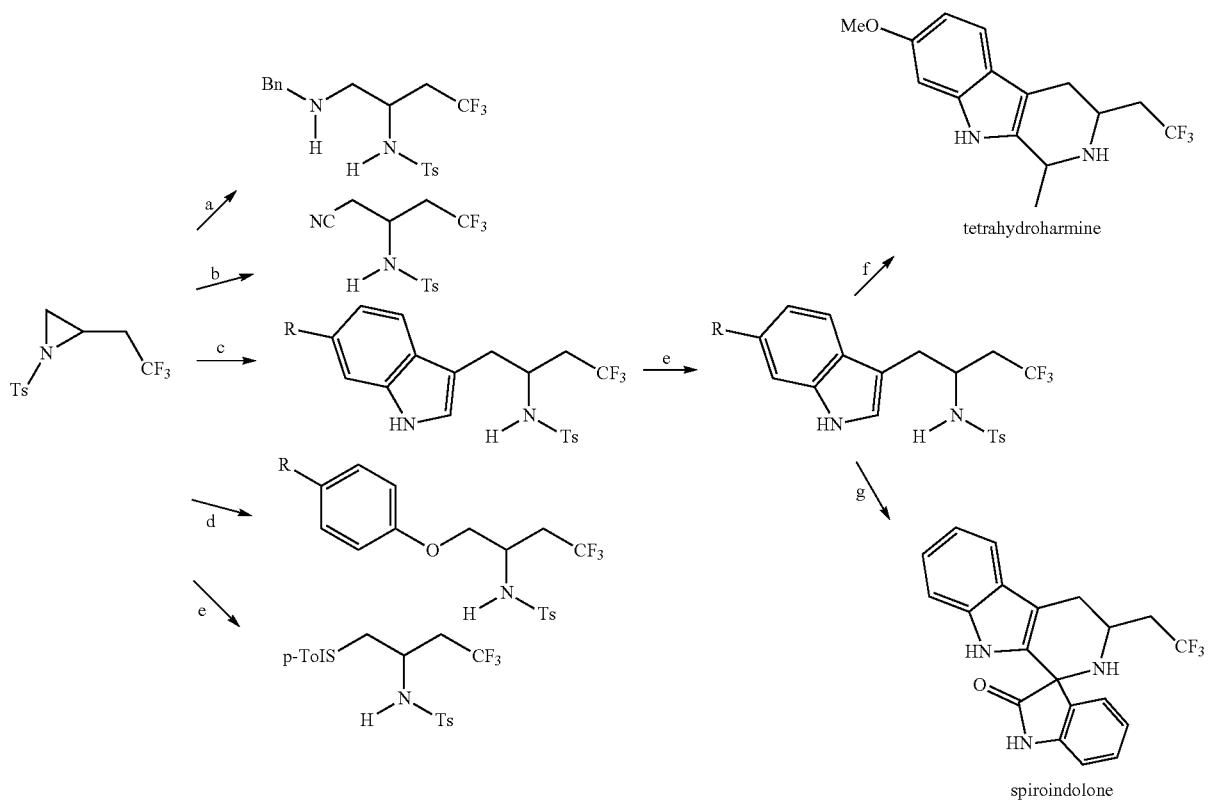

a) BnNH$_2$/MeCN, reflux; 87% b) TMSCN, TTMPP (10 mol %)/DMF, rt; 44% c) Et$_2$ZN, indole/o-xylene, reflux; R = OMe 77%, R = H, 87% d) ArOH, Cs$_2$CO$_3$/toluene, reflux; R = Me 78%, R = Br, 31%, R = I, 62% e) p-TolSH, K$_2$CO$_3$/DMF, rt; 68% e) SmI$_2$, H$_2$O, pyrrolidine/THF, rt: R = OMe 87%, R = H 85%
f) CH$_3$CHO, cat. TsOH/EtOH, 70° C., 18 h; 39% g) isatine, cat. TsOH/70° C., 15 h; 71%

(Example 7) Trifluoromethylation of Aromatic Compound (1) The reaction was conducted under the same reaction conditions as in Example 1 except that the substrate used was tert-butylbenzene. The yield was determined by GCMS analysis.

The results are shown in below.

TABLE 5

| | [Cu(CH$_3$CN)$_4$]PF$_6$ (10 mol %) | |
|---|---|---|
| TFAA (10 equiv) + urea·H$_2$O$_2$ (1.2 equiv) | CH$_2$Cl$_2$ −40° C., 1 h | t-Bu—C$_6$H$_5$ CH$_2$Cl$_2$ (0.4 M) 40° C., 3 h → t-Bu—C$_6$H$_4$—CF$_3$ |

| Entry | Cat. loading | Yield (%) (o-/m-/p-) | RSM (%) |
|---|---|---|---|
| 1 | 20 mol % | 62 (57/35/8) | 33 |
| 2 | 10 mol % | 52 (75/34/8) | 45 |
| 3 | none | 20 (57/35/8) | 77 |
| 4* | none | 63 (57/34/9) | 34 |

*The reaction was conducted for 13 h.

The yield in the absence of a copper catalyst was 20% (o-:m-:p-=57:35:8), whereas when the reaction was conducted in the presence of 20 mol % of a copper catalyst, the target product was obtained at a good yield of 62% (o-:m-:p-=57:35:8). It was also found that when the reaction time was longer even in the absence of a copper catalyst, the target product was obtained at a yield equivalent to that in the presence of a copper catalyst. This shows that the reaction time can be reduced by using the copper catalyst.

(2) The reaction was conducted in the absence of dichloromethane, a solvent for entry No. 2 in Table 5 of the above (1). As a result, the target product was obtained at a good yield of 69% (o-:m-:p-=57:34:9) as shown below.

[Formula 10]

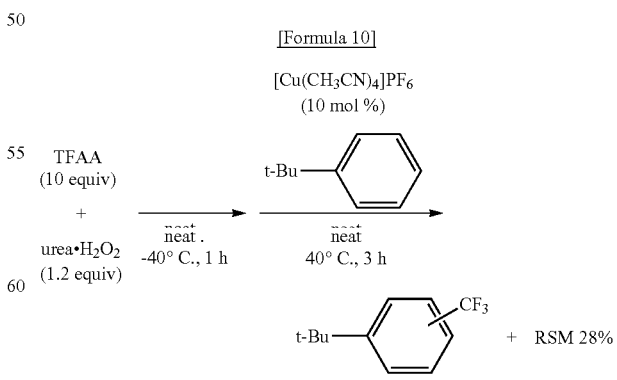

69% yield
(o-:m-:p- = 57:34:9)

(Example 8) Synthesis of Perfluoroalkylated Cyclic Compound (1) The reaction was conducted in the same manner as in Example 1 in the presence and absence of [Cu(CH$_3$CN)$_4$]PF$_6$ by using 5-(p-tolyl)-1-pentene (concentration: 0.2 M) instead of 4-pentenyl benzoate. As a result, as shown below, intramolecular cyclization occurred simultaneously with perfluoroalkylation in the absence of a copper catalyst, and a trifluoromethylated cyclic compound 3c was obtained at a good yield.

[Formula 11]

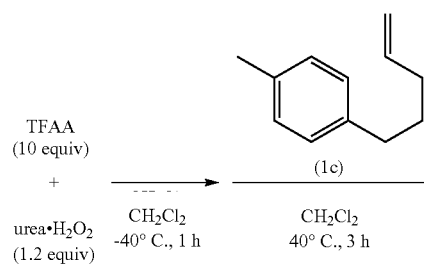

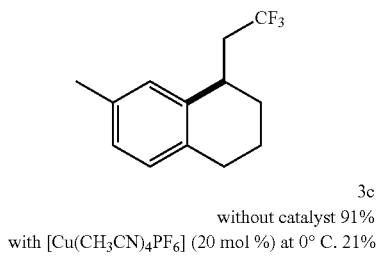

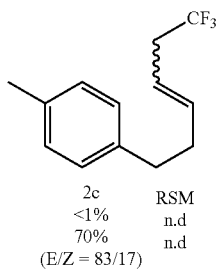

(2) Various perfluoroalkylated cyclic compounds as shown below were obtained by replacing 5-(p-tolyl)-1-pentene in the above (1) with other compounds having a terminal double bond together with an aromatic ring.

[Formula 12]

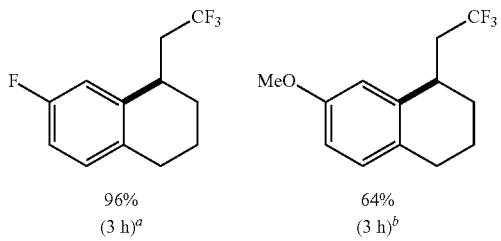

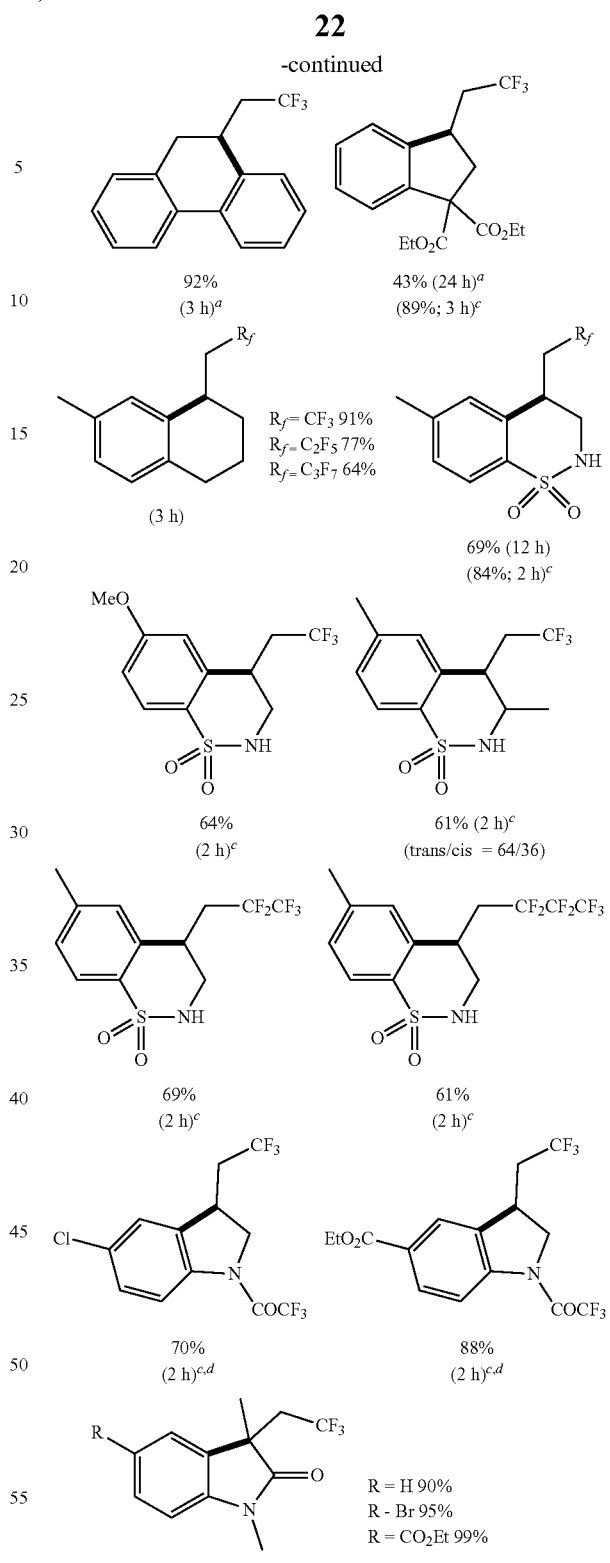

a: Substrate concentration: 0.4 M
b: Substrate concentration: 0.02 M
c: In 1,2-dichloroethane as a solvent at a reaction tempuratre of 60° C.
d: Unprotected 2-allylaniline was used as a subtrate.

Among the compounds synthesized in the above Examples, compounds which are novel substances will be shown below for their compound names, structural formulas and physical properties.

1-Methyl-4-(6,6,6-trifluoro-3-hexenyl)benzene (2c)

[Formula 13]

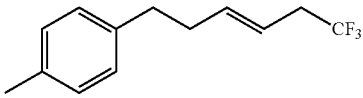

$^1$H NMR (400 MHz, CDCl$_3$)
2.30-2.40 (overlap, 5H), 2.66 (m, 2H), 2.76 (m, 2H), 5.41 (E-isomer, dt, J=15.4, 7.1 Hz; Z-isomer, overlap, 1H), 5.74 (E-isomer, dt, J=15.4, 6.8 Hz, 1H; Z-isomer, overlap, 1H), 7.05-7.30 (overlap, 4H)
$^{13}$C NMR (E-isomer; 100 MHz, CDCl$_3$)
21.1, 34.5, 35.1, 37.5 (q, J=28.9 Hz), 118.3 (q, J=3.9 Hz), 126.2 (q, J=276 Hz), 128.4 (2C), 129.2 (2C), 135.5, 137.6, 138.4
$^{19}$F NMR (376 MHz, CDCl$_3$)
E-isomer, −66.5 (t, 10.8 Hz); Z-isomer, −66.1 (t, 10.8 Hz)

15,15,15-Trifluoro-12-pentadecen-2-one (2d)

[Formula 14]

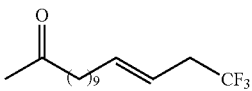

$^1$H NMR (400 MHz, CDCl$_3$)
1.20-1.43 (overlap, 12H), 1.56 (m, 2H), 2.04 (m, 2H), 2.13 (s, 3H), 2.42 (t, J=7.4 Hz, 2H), 2.76 (E-isomer, m, 2H), 2.84 (Z-isomer, m, 2H), 5.36 (E-isomer, dtt, J=15.2, 7.0, 1.5 Hz, 1H; Z-isomer, overlap, 1H), 5.68 (E-isomer, dt, J=15.2, 7.1 Hz, 1H; Z-isomer, overlap, 1H)
$^{13}$C NMR (E-isomer, 100 MHz, CDCl$_3$)
24.0, 29.0, 29.1, 29.3, 29.5 (3C), 29.9, 32.4, 37.5 (q, J=28.9 Hz), 43.9, 117.6 (q, J=3.9 Hz), 126.2 (q, J=276 Hz), 138.6, 209.5
$^{19}$F NMR (376 MHz, CDCl$_3$)
E-isomer, −66.6 (t, 10.8 Hz); Z-isomer, −66.1 (t, 10.8 Hz)

N-Phenyl-N-(6,6,6-trifluoro-3-hexenyl)trifluoroacetamide (2h)

[Formula 15]

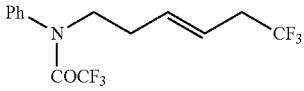

$^1$H NMR (400 MHz, CDCl$_3$)
2.36 (E-isomer, m, 2H), 2.39 (Z-isomer, m, 2H), 2.72-2.88 (m, 2H), 3.79 (Z-isomer, t, J=7.7 Hz, 2H), 3.83 (E-isomer, t, J=7.2 Hz, 2H), 5.48 (E-isomer, dtt, J=15.4, 7.0, 1.4 Hz, 1H), 5.54 (Z-isomer, dtt, J=10.9, 7.4, 1.6 Hz, 1H), 5.67 (E-isomer, dt, J=15.4, 7.0 Hz, 1H; Z-isomer, overlap, 1H), 7.18-7.24 (m, 2H), 7.40-7.49 (m, 3H)
$^{13}$C NMR (E-isomer, 100 MHz, CDCl$_3$) 30.3, 37.4 (q, J=29.9 Hz), 50.8, 116.4 (q, J=288 Hz), 121.0 (q, J=2.9 Hz), 125.9 (q, J=276 Hz), 128.5 (2C), 129.3 (2C), 129.6, 133.8, 138.9, 156.8 (q, J=35.6 Hz)
$^{19}$F NMR (376 MHz, CDCl$_3$)
E-isomer, −67.2 (s, 3F), −66.5 (t, 11.6 Hz, 3F) Z-isomer, −67.2 (s, 3F), −66.1 (t, 11.6 Hz, 3F)

4-Methyl-N-(7,7,7-trifluoro-4-heptenyl)benzenesulfonamide (2i)

[Formula 16]

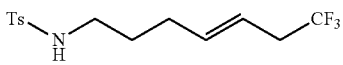

$^1$H NMR (400 MHz, CDCl$_3$)
1.57 (m, 2H), 2.06 (m, 2H), 2.43 (s, 3H), 2.68-2.85 (m, 2H), 2.90-2.98 (m, 2H), 4.35-4.53 (br, 1H), 5.34 (E-isomer, m, 1H), 5.41 (Z-isomer, m, 1H), 5.60 (E-isomer, dt, J=15.4, 6.6 Hz, 1H; Z-isomer, overlap, 1H), 7.31 (d, J=8.1 Hz, 2H), 7.74 (d, J=8.1 Hz, 2H)
$^{13}$C NMR (E-isomer, 100 MHz, CDCl$_3$)
21.6, 28.8, 29.4, 37.3 (q, J=28.9 Hz), 42.5, 118.9 (q, J=2.9 Hz), 126.0 (q, J=276 Hz), 127.2 (2C), 129.8 (2C), 136.7, 137.0, 143.6
$^{19}$F NMR (376 MHz, CDCl$_3$)
E-isomer, −66.5 (t, 10.8 Hz); Z-isomer, −66.0 (t, 10.8 Hz)

4-Methyl-N-(7,7,8,8,8-pentafluoro-4-octenyl)benzenesulfonamide (2i')

[Formula 17]

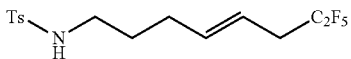

$^1$H NMR (400 MHz, CDCl$_3$)
1.56 (m, 2H), 2.07 (m, 2H), 2.43 (s, 3H), 2.62-2.83 (m, 2H), 2.90-2.96 (m, 2H), 4.70-4.76 (br, 1H), 5.34 (E-isomer, dt, J=15.3, 7.2 Hz, 1H), 5.41 (Z-isomer, br, 1H), 5.60 (E-isomer, dt, J=15.3, 6.9 Hz, 1H; Z-isomer, overlap, 1H), 7.31 (d, J=8.4 Hz, 2H), 7.75 (d, J=8.4 Hz, 2H)
$^{13}$C NMR (E-isomer, 100 MHz, CDCl$_3$) (The carbons of the perfluoroalkyl group could not be assigned because of low intensity of signals and their complex coupling.)
21.6, 28.9, 29.5, 34.5 (t, J=22.2 Hz), 42.6, 117.9 (t, J=3.9 Hz), 127.2 (2C), 129.8 (2C), 135.4, 137.2, 143.6
$^{19}$F NMR (376 MHz, CDCl$_3$)
E-isomer, −117.2 (m, 2F), −84.7 (m, 3F); Z-isomer, −116.9 (m, 2F) −84.8 (m, 3F)

4-Methyl-N-(7,7,8,8,9,9,9-heptafluoro-4-nonenyl)benzenesulfonamide (2i")

[Formula 18]

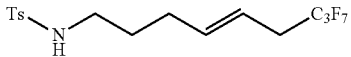

$^1$H NMR (400 MHz, CDCl$_3$)
1.57 (m, 2H), 2.06 (m, 2H), 2.42 (s, 3H), 2.65-2.87 (m, 2H), 2.88-2.98 (m, 2H), 4.92 (br, 1H), 5.34 (E-isomer, dt, J=15.4, 7.1 Hz, 1H; Z-isomer, overlap, 1H), 5.60 (E-isomer, dt, J=15.4, 6.9 Hz, 1H; Z-isomer, overlap, 1H), 7.30 (d, J=8.1 Hz, 2H), 7.76 (d, J=8.1 Hz, 2H)

$^{13}$C NMR (E-isomer, 100 MHz, CDCl$_3$) (The carbons of the perfluoroalkyl group could not be assigned because of low intensity of signals and their complex coupling.)

21.5, 28.8, 29.5, 34.5 (t, J=22.2 Hz), 42.5, 117.7 (t, J=4.9 Hz), 127.2 (2C), 129.8 (2C), 135.6, 137.4, 143.6

$^{19}$F NMR (376 MHz, CDCl$_3$)

E-isomer, −127.4 (m, 2F), −114.2 (m, 2F), −80.6 (m, 3F); Z-isomer, −127.2 (m, 2F), −113.9 (m, 2F), −80.5 (m, 3F)

7-Fluoro-1-(2,2,2-trifluoroethyl)-1,2,3,4-tetrahydronaphtalene (3j)

[Formula 19]

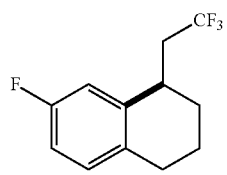

$^1$H NMR (400 MHz, CDCl$_3$)

1.77-1.94 (m, 4H), 2.30-2.51 (m, 2H), 2.66-2.79 (m, 2H), 3.18 (m, 1H), 6.80-6.87 (m, 2H), 7.03 (dd, J=9.4, 6.2 Hz, 1H)

$^{13}$C NMR (100 MHz, CDCl$_3$)

18.9, 27.7, 28.7, 32.5 (br), 40.8 (q, J=27.0 Hz), 113.7 (d, J=21.2 Hz), 114.8 (d, J=20.2 Hz), 126.9 (q, J=277 Hz), 130.9 (d, J=7.7 Hz), 132.7 (d, J=2.9 Hz), 140.5 (d, J=6.7 Hz), 161.2 (d, J=244 Hz)

$^{19}$F NMR (376 MHz, CDCl$_3$)

−63.8 (t, J=11.6 Hz, 3F), −116.9 (m, 1F)

7-Methoxy-1-(2,2,2-trifluoroethyl)-1,2,3,4-tetrahydronaphtalene (3k)

[Formula 20]

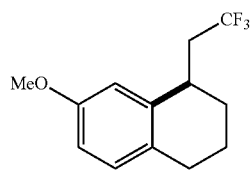

$^1$H NMR (400 MHz, CDCl$_3$)

1.73-1.99 (m, 4H), 2.30-2.52 (m, 2H), 2.62-2.79 (m, 2H), 3.13-3.22 (m, 1H), 3.78 (s, 3H), 6.66 (d, J=2.6 Hz, 1H), 6.72 (dd, J=8.4, 2.6 Hz, 1H), 6.99 (d, J=8.4 Hz, 1H)

$^{13}$C NMR (100 MHz, CDCl$_3$)

19.3, 27.8, 28.6, 32.6 (q, J=1.9 Hz), 40.9 (q, J=27.0 Hz), 55.4, 112.7, 113.5, 127.1 (q, J=277 Hz), 129.3, 130.4, 139.8, 157.9

$^{19}$F NMR (376 MHz, CDCl$_3$)

−63.8 (t, 11.6 Hz)

7-Methyl-1-(2,2,3,3,3-pentafluoropropyl)-1,2,3,4-tetrahydronaphtalene (3c')

[Formula 21]

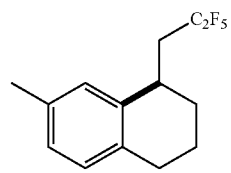

$^1$H NMR (400 MHz, CDCl$_3$)

1.73-2.01 (m, 4H), 2.20-2.49 (m, 5H), 2.63-2.80 (m, 2H), 3.21-3.34 (m, 1H), 6.90-6.99 (m, 3H)

$^{13}$C NMR (100 MHz, CDCl$_3$) (The carbons of the perfluoroalkyl group could not be assigned because of low intensity of signals and their complex coupling.)

19.2, 21.1, 28.4 (m), 28.9, 31.1 (br), 37.5 (t, J=20.2 Hz), 127.4, 129.3, 129.5, 134.2, 135.8, 138.8

$^{19}$F NMR (376 MHz, CDCl$_3$)

−117.0 (m, 2F), −85.6 (m, 3F)

7-Methyl-1-(2,2,3,3,4,4,4-heptafluorobutyl)-1,2,3,4-tetrahydronaphtalene (3c")

[Formula 22]

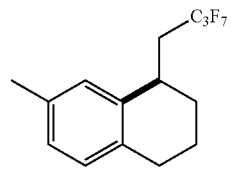

$^1$H NMR (400 MHz, CDCl$_3$)

1.73-2.01 (m, 4H), 2.25-2.50 (m, 5H), 2.64-2.81 (m, 2H), 3.23-3.37 (m, 1H), 6.88-6.99 (m, 3H)

$^{13}$C NMR (100 MHz, CDCl$_3$) (The carbons of the perfluoroalkyl group could not be assigned because of low intensity of signals and their complex coupling.)

19.2, 21.2, 28.5 (m), 31.0 (br), 37.4 (t, J=20.2 Hz), 127.4, 129.3, 129.5, 134.2, 135.8, 138.8 $^{19}$F NMR (376 MHz, CDCl$_3$)

−127.7 (m, 2F), −114.0 (m, 2F), −80.3 (m, 3F)

1-Tosyl-2-(2,2,2-trifluoroethyl)aziridine

[Formula 23]

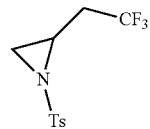

¹H NMR (400 MHz, CDCl₃)

2.16 (d, J=4.3 Hz, 1H), 2.16-2.40 (m, 2H), 2.45 (s, 3H), 2.75 (d, J=7.0 Hz, 1H), 2.89-2.95 (m, 1H), 7.36 (d, J=8.0 Hz, 2H), 7.82 (d, J=8.0 Hz, 2H)

¹³C NMR (100 MHz, CDCl₃)

21.8, 31.9, 32.0 (q, J=3.9 Hz), 36.3 (q, J=29.9 Hz), 125.3 (q, J=277 Hz), 128.3 (2C), 129.9 (2C), 134.5, 145.2

¹⁹F NMR (376 MHz, CDCl₃)

−65.3 (t, J=10.1 Hz)

1-((4-Methoxyphenyl)sulfonyl)-2-(2,2,2-trifluoro-ethyl)aziridine

[Formula 24]

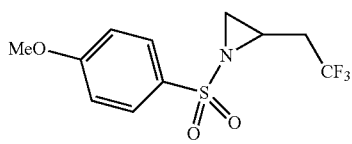

¹H NMR (400 MHz, CDCl₃)

2.16 (d, J=4.4 Hz, 1H), 2.18-2.34 (m, 2H), 2.73 (d, J=6.9 Hz, 1H), 2.86-2.92 (m, 1H), 3.90 (s, 3H), 7.02 (d, J=9.0 Hz, 2H), 7.87 (d, J=9.0 Hz, 2H)

¹³C NMR (100 MHz, CDCl₃)

31.9, 33.0 (q, J=3.9 Hz), 36.3 (q, J=29.9 Hz), 56.8, 114.5 (2C), 125.3 (q, J=277 Hz), 128.8, 130.5 (2C), 164.1

¹⁹F NMR (376 MHz, CDCl₃)

−65.3 (t, J=10.1 Hz)

1-((4-Bromophenyl)sulfonyl)-2-(2,2,2-trifluoroethyl)aziridine

[Formula 25]

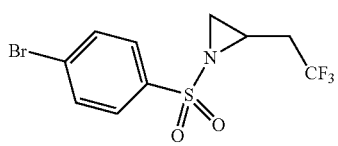

¹H NMR (400 MHz, CDCl₃)

2.20 (d, J=4.4 Hz, 1H), 2.23-2.32 (m, 2H), 2.79 (d, J=7.0 Hz, 1H), 2.94-3.00 (m, 1H), 7.71 (d, J=8.7 Hz, 2H), 7.81 (d, J=8.7 Hz, 2H)

¹³C NMR (100 MHz, CDCl₃)

32.0, 33.4 (q, J=4.8 Hz), 36.3 (q, J=29.9 Hz), 125.2 (q, J=275 Hz), 129.4, 129.7 (2C), 132.6 (2C), 136.6

¹⁹F NMR (376 MHz, CDCl₃)

−65.3 (t, J=10.1 Hz)

1-((4-Fluorophenyl)sulfonyl)-2-(2,2,2-trifluoroethyl)aziridine

[Formula 26]

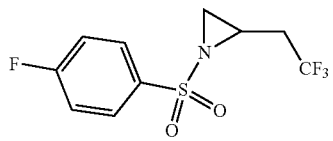

¹H NMR (400 MHz, CDCl₃)

2.20 (d, J=4.4 Hz, 1H), 2.22-2.32 (m, 2H), 2.80 (d, J=7.0 Hz, 1H), 2.92-2.98 (m, 1H), 7.21-7.27 (m, 2H), 7.95-8.00 (m, 2H)

¹³C NMR (100 MHz, CDCl₃)

32.0, 33.4 (q, J=3.9 Hz), 36.3 (q, J=28.9 Hz), 116.7 (d, J=23.1 Hz, 2C), 125.1 (q, J=277 Hz), 131.1 (d, J=9.6 Hz, 2C), 133.6, 156.7

¹⁹F NMR (376 MHz, CDCl₃)

−65.3 (t, J=10.1 Hz, 3H), −102.8 (m, 1H)

1-Mesyl-2-(2,2,2-trifluoroethyl)aziridine

[Formula 27]

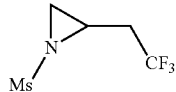

¹H NMR (400 MHz, CDCl₃)

2.18 (d, J=4.4 Hz, 1H), 2.21-2.50 (m, 2H), 2.72 (d, J=7.1 Hz, 1H), 2.86-2.94 (m, 1H), 3.08 (s, 3H)

¹³C NMR (100 MHz, CDCl₃)

30.5, 33.1 (q, J=3.9 Hz), 36.3 (q, J=28.9 Hz), 39.7, 125.5 (q, J=277 Hz)

¹⁹F NMR (376 MHz, CDCl₃)

−65.0 (t, J=10.1 Hz)

7-Tosyl-2-(trifluoromethyl)-7-azabicyclo[4.1.0]heptane

[Formula 28]

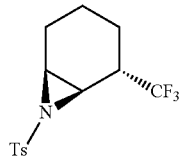

¹H NMR (400 MHz, CDCl₃)

1.11-1.40 (m, 2H), 1.50-1.60 (m, 1H), 1.65-1.80 (m, 2H), 1.99-2.10 (m, 1H), 2.28-2.41 (m, 1H), 2.45 (s, 3H), 2.97 (d, J=7.0 Hz, 1H), 3.13 (m, 1H), 7.35 (d, J=8.1 Hz, 2H), 7.80 (d, J=8.1 Hz, 2H)

¹³C NMR (100 MHz, CDCl₃)
16.4, 20.5 (q, J=1.9 Hz), 21.8, 22.6, 37.3 (q, J=3.9 Hz), 39.1, 39.2 (q, J=27.0 Hz), 126.8 (q, J=279 Hz), 127.9 (2C), 129.9 (2C), 135.1, 144.8

¹⁹F NMR (376 MHz, CDCl₃)
−72.0 (d, J=10.1 Hz)

2-(2,2,3,3,3-Pentafluoropropyl)-1-tosylaziridine

[Formula 29]

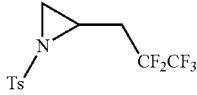

¹H NMR (400 MHz, CDCl₃)
2.03-2.15 (m, 1H), 2.17 (d, J=4.3 Hz, 1H), 2.29-2.43 (m, 1H), 2.46 (s, 3H), 2.76 (d, J=6.9 Hz, 1H), 2.97-3.04 (m, 1H), 7.36 (d, J=8.0 Hz, 2H), 7.83 (d, J=8.0 Hz, 2H)

¹³C NMR (100 MHz, CDCl₃) (The carbons of the perfluoroalkyl group could not be assigned because of low intensity of signals and their complex coupling.)
21.8, 32.2 (t, J=5.8 Hz), 32.3, 33.5 (t, J=22.2 Hz), 128.2 (2C), 130.0 (2C), 134.5, 145.2

¹⁹F NMR (376 MHz, CDCl₃)
−85.4 (m, 3F), −117.3 (m, 2F)

2-(2,2,3,3,4,4,4-Heptafluorobutyl)-1-tosylaziridine

[Formula 30]

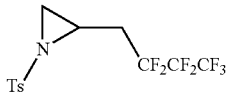

¹H NMR (400 MHz, CDCl₃)
2.06-2.23 (m, 1H), 2.17 (d, J=4.8 Hz, 1H), 2.30-2.42 (m, 1H), 2.46 (s, 3H), 2.76 (d, J=7.0 Hz, 1H), 2.98-3.05 (m, 1H), 7.36 (d, J=8.0 Hz, 2H), 7.83 (d, J=8.0 Hz, 2H)

¹³C NMR (100 MHz, CDCl₃) (The carbons of the perfluoroalkyl group could not be assigned because of low intensity of signals and their complex coupling.)
21.8, 32.1 (t, J=4.8 Hz), 32.2, 33.6 (t, J=21.2 Hz), 128.2 (2C), 129.9 (2C), 134.5, 145.0

¹⁹F NMR (376 MHz, CDCl₃)
−80.4 (m, 3F), −114.3 (m, 2F), −127.5 (m, 2F)

1-Mesyl-2-(2,2,2-trifluoroethyl)pyrrolidine

[Formula 31]

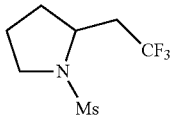

¹H NMR (400 MHz, CDCl₃)
1.87-2.01 (overlap, 3H), 2.14 (m, 1H), 2.24 (m, 1H), 2.85 (overlap, 4H), 3.31 (m, 1H), 3.41 (m, 1H), 3.89 (m, 1H)

¹³C NMR (100 MHz, CDCl₃)
24.6, 31.8 (q, J=1.2 Hz), 35.0, 40.3 (q, J=27.0 Hz), 48.8, 54.8 (q, J=2.9 Hz), 125.6 (q, J=277 Hz)

¹⁹F NMR (376 MHz, CDCl₃)
−63.5 (t, J=10.9 Hz)

1-Tosyl-2-(2,2,2-trifluoromethyl)octahydro-1-indole

[Formula 32]

¹H NMR (400 MHz, CDCl₃)
0.91-1.42 (overlap, 6H), 1.63 (m, 1H), 1.80 (m, 2H), 2.21-2.35 (m, 2H), 2.36-2.43 (overlap, 4H), 2.80 (m, 1H), 3.27 (m, 1H), 4.15 (m, 1H), 7.28 (d, J=8.2 Hz, 2H), 7.70 (d, J=8.2 Hz, 2H)

¹³C NMR (100 MHz, CDCl₃)
21.7, 25.1, 25.2, 29.4, 29.9, 37.8, 41.3 (q, J=27.0 Hz), 42.9, 55.5 (q, J=2.9 Hz), 66.0, 126.1 (q, J=277 Hz), 127.2 (2C), 129.8 (2C), 139.4, 143.3

¹⁹F NMR (376 MHz, CDCl₃)
−63.1 (t, J=11.0 Hz)

(Diastereomer)

¹H NMR (400 MHz, CDCl₃)
0.91-1.42 (overlap, 6H), 1.70 (m, 1H), 1.80 (overlap, 3H), 2.21-2.25 (m, 2H), 245 (s, 3H), 2.55 (m, 1H), 2.88 (m, 1H), 3.77 (m, 1H), 7.35 (d, J=7.8 Hz, 2H), 7.68 (overlap, 2H)

¹³C NMR (100 MHz, CDCl₃)
21.7, 24.7, 25.4, 29.6, 32.8, 34.5, 41.2 (q, J=27.0 Hz), 42.9, 55.1 (q, J=2.9 Hz), 66.5, 126.1 (q, =J=277 Hz), 128.0 (2C), 129.9 (2C), 132.9, 144.0

¹⁹F NMR (376 MHz, CDCl₃)
−63.7 (t, J=11.0 Hz)

5-Chloro-1-tosyl-2-(2,2,2-trifluoroethyl)indole

[Formula 33]

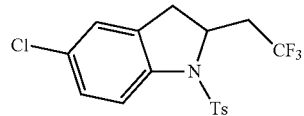

¹H NMR (400 MHz, CDCl₃)
2.38 (s, 3H), 2.44 (m, 1H), 2.76 (dd, J=16.8, 3.3 Hz, 1H), 2.88-2.99 (overlap, 2H), 4.42 (m, 1H), 7.03 (m, 1H), 7.21 (overlap, 3H), 7.54 (d, J=8.3 Hz, 2H), 7.62 (d, J=8.6 Hz, 1H)

¹³C NMR (100 MHz, CDCl₃)
21.7, 34.1 (q, J=1.5 Hz), 40.7 (q, J=26.9 Hz), 57.2 (q, J=3.2 Hz), 118.3, 125.6, 125.6 (q, J=276 Hz), 127.3 (2C), 128.4, 130.1 (2C), 130.5, 132.7, 133.9, 139.6, 144.8

¹⁹F NMR (376 MHz, CDCl₃)
−62.9 (t, J=10.9 Hz)

4-(2,2,3,3,3-Pentafluoropropyl)-6-methyl-1,2-benzothiazinane Dioxide

[Formula 34]

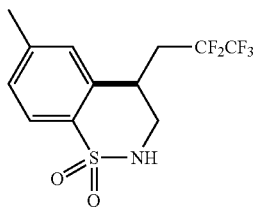

¹H NMR (400 MHz, CDCl₃)

2.32-2.61 (m, 2H), 2.41 (s, 3H), 3.31-3.36 (m, 1H), 3.73 (m, 1H), 4.08 (m, 1H), 4.76 (m, 1H), 7.06 (s, 1H), 7.26 (d, J=8.2 Hz, 1H), 7.74 (d, J=8.2 Hz, 1H)

¹³C NMR (100 MHz, CDCl₃) (The carbons of the perfluoroalkyl group could not be assigned because of low intensity of signals and their complex coupling.)

21.7, 31.1, 34.9 (t, J=21.1 Hz), 45.3, 124.8, 129.4, 129.7, 135.0, 137.3, 143.8

¹⁹F NMR (376 MHz, CDCl₃)

−85.4 (m, 3F), −116.6 (m, 2F)

4-(2,2,3,3,4,4,4-Heptafluorobutyl)-6-methyl-1,2-benzothiazinane Dioxide

[Formula 35]

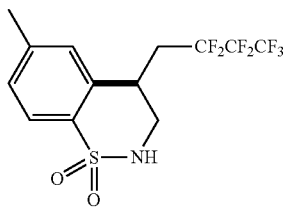

¹H NMR (400 MHz, CDCl₃)

2.40-2.64 (m, 2H), 2.41 (s, 3H), 3.33-3.38 (m, 1H), 3.73 (m, 1H), 4.07 (m, 1H), 4.70 (m, 1H), 7.06 (s, 1H), 7.27 (d, J=8.0 Hz, 1H), 7.75 (d, J=8.0 Hz, 1H)

¹³C NMR (100 MHz, CDCl₃) (The carbons of the perfluoroalkyl group could not be assigned because of low intensity of signals and their complex coupling.)

21.7, 31.0, 34.9 (t, J=21.1 Hz), 45.4, 124.8, 129.4, 129.7, 135.0, 137.3, 143.8

¹⁹F NMR (376 MHz, CDCl₃)

−80.1 (m, 3F), −113.4 (m, 2F), −127.3 (m, 2F)

1-Trifluoroacetyl-5-chloro-3-(2,2,2-trifluoroethyl)indoline

[Formula 36]

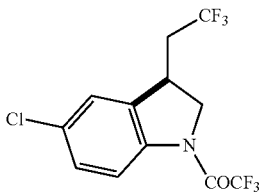

¹H NMR (400 MHz, CDCl₃)

2.30-2.45 (m, 1H), 2.60-2.75 (m, 1H), 3.74-3.86 (m, 1H), 4.09 (dd, J=11.6, 6.8 Hz, 1H), 4.51 (m, 1H), 7.25 (m, 1H), 7.31 (dd, J=8.7, 2.1 Hz, 1H), 8.73 (d, J=8.7 Hz, 1H)

¹³C NMR (100 MHz, CDCl₃)

35.1, 38.5 (q, J=28.9 Hz), 54.0 (q, J=1.9 Hz), 116.0 (q, J=287 Hz), 119.2, 124.3, 126.0 (q, J=277 Hz), 129.3, 131.6, 134.3, 140.0, 154.2 (q, J=38.5 Hz)

¹⁹F NMR (376 MHz, CDCl₃)

−64.6 (t, J=10.1 Hz, 3F), −72.4 (s, 3F)

1-Trifluoroacetyl-5-ethoxycarbonyl-3-(2,2,2-trifluoroethyl)indoline

[Formula 37]

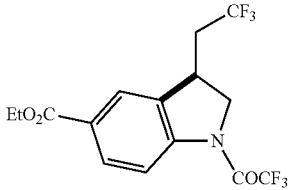

¹H NMR (400 MHz, CDCl₃)

1.39 (t, J=7.1 Hz, 3H), 2.03-2.45 (m, 1H), 2.69-2.82 (m, 1H), 3.38 (m, 1H), 4.12 (m, 1H), 4.37 (q, J=7.1 Hz, 2H), 4.54 (m, 1H), 7.92 (s, 1H), 8.04 (d, J=8.5 Hz, 1H), 8.24 (d, J=8.5 Hz, 1H)

¹³C NMR (100 MHz, CDCl₃)

14.5, 35.0, 38.6 (q, J=28.9 Hz), 54.0 (q, J=1.9 Hz), 61.5, 115.9 (q, J=288 Hz), 117.8, 125.3, 126.1 (q, J=277 Hz), 128.5, 131.4, 132.8, 145.0, 154.5 (q, J=38.5 Hz), 165.7

¹⁹F NMR (376 MHz, CDCl₃)

−64.6 (t, J=10.1 Hz, 3F), −72.5 (s, 3F)

All publications, patents and patent applications cited in the present specification are incorporated herein by reference in their entirety.

The invention claimed is:

1. An aziridine derivative represented by formula (V-1):

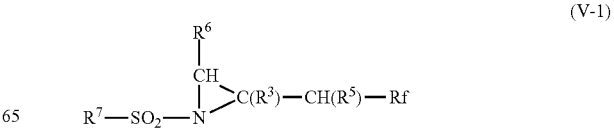

wherein Rf represents a perfluoroalkyl group having 1 to 6 carbon atoms, $R^3$, $R^5$ and $R^6$, which are the same or different, each represent a hydrogen atom or a substituted or unsubstituted $C_{1-6}$-alkyl group, $R^5$ and $R^6$ may be linked to form a 5- to 7-membered carbon ring together with CH—C($R^3$)—CH to which they are attached, and $R^7$ represents a substituted or unsubstituted $C_{1-6}$-alkyl group or a substituted or unsubstituted phenyl group.

2. A method for producing the aziridine derivative according to claim 1, comprising reacting a bis(perfluoroalkanoyl) peroxide represented by formula (I):

Rf—CO—OO—CO—Rf  (I)

wherein Rf represents a perfluoroalkyl group having 1 to 6 carbon atoms, with a compound represented by formula (IVa):

$R^7$—SO$_2$—NH—CH($R^6$)—C($R^3$)=CH($R^5$)  (IVa)

wherein $R^3$, $R^5$, $R^6$, and $R^7$ are as defined in claim 1, in the presence of a copper catalyst.

3. The method according to claim 2, wherein the bis (perfluoroalkanoyl) peroxide is produced from perfluoroalkanoic anhydride and a urea-hydrogen peroxide complex.

4. The method according to claim 2, wherein the copper catalyst is [Cu(CH$_3$CN)$_4$]PF$_6$.

5. The aziridine derivative according to claim 1, wherein $R^3$, $R^5$ and $R^6$, which are the same or different, each represent a hydrogen atom or a $C_{1-6}$-alkyl group, $R^5$ and $R^6$ may be linked to form a 5- to 7-membered carbon ring together with CH—C($R^3$)—CH to which they are attached, and $R^7$ represents a $C_{1-6}$-alkyl group or a phenyl group, wherein the $C_{1-6}$-alkyl group may be substituted with one or more substituents selected from a halogen atom, a hydroxyl group, an amino group, a mono- or dialkylamino group, a $C_{1-6}$-alkoxy group, an oxo group, an aromatic group, and a heterocyclic group, and the phenyl group may be substituted with one or more substituents selected from a methyl group, a methoxy group, a fluorine atom, a bromine atom, and a nitro group.

6. The aziridine derivative according to claim 1, wherein $R^3$, $R^5$ and $R^6$, which are the same or different, each represent a hydrogen atom or a $C_{1-6}$-alkyl group, $R^5$ and $R^6$ may be linked to form a 5- to 7-membered carbon ring together with CH—C($R^3$)—CH to which they are attached, and $R^7$ represents a $C_{1-6}$-alkyl group, a phenyl group, a tolyl group, a 4-methoxyphenyl group, a 4-fluorophenyl group, a 4-bromophenyl group, or a 4-nitrophenyl group, wherein the $C_{1-6}$-alkyl group may be substituted with one or more substituents selected from a halogen atom, a hydroxyl group, an amino group, a mono- or dialkylamino group, a $C_{1-6}$alkoxy group, an oxo group, an aromatic group, and a heterocyclic group.

* * * * *